United States Patent
Fan et al.

(10) Patent No.: US 6,172,129 B1
(45) Date of Patent: Jan. 9, 2001

(54) CYCLIC AMINE ACRYLATE MONOMERS AND POLYMERS

(75) Inventors: Ming Xin Fan, West Chester; Gary Ceska, Exton; James P. Horgan, West Chester; Henry C. Miller, Downingtown; Edward A. Jurczak, Elkins, all of PA (US)

(73) Assignee: Sartomer Technologies, Inc., Exton, PA (US)

( * ) Notice: Under 35 U.S.C. 154(b), the term of this patent shall be extended for 0 days.

(21) Appl. No.: 09/240,940

(22) Filed: Jan. 29, 1999

(51) Int. Cl.[7] .............................. C08F 2/48; C08F 26/06; C07D 413/00; C07D 265/30; C07D 295/18

(52) U.S. Cl. ......................... 522/167; 522/173; 522/103; 526/258; 526/260; 526/263; 252/182.13; 252/182.18; 544/106; 544/129; 544/130; 544/171; 546/248; 546/184

(58) Field of Search ..................................... 522/167, 173, 522/103; 544/106, 129, 130, 131, 171; 546/248, 184; 560/205; 526/258, 260, 263; 252/182.13, 182.18

(56) References Cited

U.S. PATENT DOCUMENTS

| 3,876,518 | * | 4/1975 | Borden et al. | 522/100 |
|---|---|---|---|---|
| 3,974,131 | | 8/1976 | Puskas . | |
| 4,039,414 | * | 8/1977 | McGinniss | 204/478 |
| 4,045,416 | * | 8/1977 | Robson et al. | 260/453 A |
| 4,886,840 | * | 12/1989 | Mukohyama et al. | 522/96 |
| 5,596,669 | | 1/1997 | Murphy . | |

FOREIGN PATENT DOCUMENTS

| 06184473 | 5/1994 | (JP) . |
|---|---|---|
| 2000109522 | 4/2000 | (JP) . |

* cited by examiner

Primary Examiner—Susan W. Berman
(74) Attorney, Agent, or Firm—Michael Fein; Cozen & O'Connor

(57) ABSTRACT

(Meth)acrylate functional compound which is the reaction product of a cyclic secondary amine and a poly(meth) acrylate having at least three acrylate or methacrylate groups, useful for radiation curable coating or ink composition having low viscosity, low volatility, and high cure rate under radiation. Process of preparing a coating or ink composition using such compound. Radiation cured coating or ink based on such composition. Coated or printed article having such a cured coating or ink based on such composition.

8 Claims, No Drawings

CYCLIC AMINE ACRYLATE MONOMERS AND POLYMERS

BACKGROUND OF THE INVENTION

1. Field of the Invention

This invention relates to aminoacrylate monomers, process for preparation of monomers and polymers, coatings, and inks made with aminoacrylate monomers.

2. Description of the Prior Art

Coatings, inks, and adhesives can be prepared from (meth)acrylate monomers and oligomers by radiation curing. Radiation curing is generally done under UV or EB radiation, optionally in the presence of photoinitiators, and proceeds by a free radical mechanism. A problem in this art is that air retards or inhibits the cure, leading to tacky surfaces. German patent DE 3706355 suggests that amines and acrylated amines can enhance the surface cure, even in the presence of oxygen. U.S. Pat. No. 3,876,518 and Canadian Pat. 1011891 teach that the modification of acrylated epoxidized soybean oil with amine at low level can enhance the surface cure which is especially useful in ink applications. Robson, et al. U.S. Pat. No. 4,045,416 assigned to Union Carbide Corporation teaches preparation of amine acrylates from primary and secondary amines and polyacrylates, preferably diacrylates and their use directly or as part of radiation curable formulations. Meixner, et al. U.S. Pat. No. 5,482,649, assigned to Bayer Ak., disclosed that the modification of acrylates with primary amines at low level leads to low viscosity aminoacrylates. U.S. Pat. No. 3,876,518 teaches low acrylate functionality for amine acrylates in radiation cure applications.

The prior art did not teach low viscosity, low volatility, high cure rate compositions comprising multifunctional acrylates. According to the prior art, it would have been expected that modification of multifunctional acrylates with amines would lead to high viscosity or gel-like materials.

An object of the present invention was to provide reactive acrylates having low viscosity which can be used in radiation, especially UV and EB, cure.

SUMMARY OF THE INVENTION

These objects, and others which will become apparent from the following disclosure, are achieved by the present invention which comprises in one aspect a (meth)acrylate (i.e., acrylate, methacrylate, or mixtures thereof) functional compound which is the reaction product of a cyclic secondary amine and a poly(meth)acrylate having at least three (meth)acrylate groups, useful for radiation curable coating or ink composition having low viscosity, low volatility, and high cure rate under radiation.

Other aspects of the invention include the process for preparing such coating and ink composition, the coatings and inks, articles coated with the coating or printed with the ink.

DETAILED DESCRIPTION OF THE INVENTION AND PREFERRED EMBODIMENTS

The multifunctional reactive amine acrylates of the invention can be prepared by reacting (meth)acrylates having at least three (meth)acrylate groups with a cyclic secondary amine compound such as morpholine and/or piperidine. The reaction between acrylates and amines is known as Michael addition reaction, both primary and secondary amines are suitable.

Multifunctional acrylates are well known in the art which can be prepared from (meth)acrylic acid and tri- or tetrahydroxy polyols in the presence of catalysts. Suitable (meth) acrylates include propoxylated glyceryl triacrylate, trimethylolpropane triacrylate, ethoxylated trimethylolpropane triacrylate, propoxylated trimethylol propane triacrylate, pentaerythritol triacrylate, tris (2-hydroxy ethyl) isocyanurate triacrylate, dipentaerythritol pentaacrylate, ditrimethylolpropane tetraacrylate, pentaerythritol tetraacrylate, ethoxylated pentaeytliritol tetraacrylate, urethane acrylates, and epoxy acrylates. The general formula for acrylates are shown below

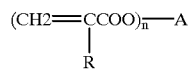

where R is hydrogen or methyl, A is the residue of a polyol, and n is an integer having a value of 3 to 6.

The production of polyacrylate esters is well known to those of normal skill in the art. It is known that an acid such as acrylic acid or methacrylic acid will react with a polyhydroxyl compound to produce the polyacrylate ester. The polyacrylate esters can also be produced by transesterification reactions. These reactions are known in the art and the conditions under which they are carried out are so well known that they need not be set forth in detail.

The polyols that are reacted with acrylic acid or methacrylic acid to produce the polyacrylate esters can be any of the compounds containing three or more hydroxyl groups that will undergo esterification. These are well known and include the aliphatic-type polyols having from three to about 20 carbon atoms, triols such as trimethylol propane, glycerol, 1,2,6-hexanetriol; tetrols such as pentaerythritrol; and the like; the ether polyols having a molecular weight of from about 106 to about 15,000, including the block polyoxyalkylene polyols.

Hence, the residue of the polyol used to produce the polyacrylate ester can be a saturated or unsaturated linear or branched polyvalent alkylene.

Suitable secondary cyclic amines include morpholine, substituted morpholines, piperidine, substituted piperidines, and the like. The preferred amines are morpholine and piperidine. The morpholine or piperidine can be modified, for example the reaction product of piperazine or alkyl substituted piperazines with mono-epoxides such as epichlorohydrin, styrene oxide, ethylene oxide, propylene oxide, butylene oxide, cyclohexane oxide, and the like, or poly-epoxides such as diglycidyl ether of bisphenol A, 4-vinyl-1-cyclohexene dioxide, and the like; the reaction product of said piperazines with an isocyanate such as phenyl isocyanate, methyl isocyanate, tolylene diisocyanate, bis(2-isocyanatoethyl)bicyclo[2.2.1]-hept-5-ene-2,3-dicarboxylate, bis(2-isocyanatoethyl)4-cyclohexene-1,2-dicarboxylate, and the like. In these instances only one of the >NH groups of the piperazine compound is reacted and there is always an >NH group available from the piperazine molecule.

The reaction between the acrylates and secondary cyclic amine can take place without any catalyst or solvent. The reaction can be carried out at temperature between −30 to 150° C., the preferred temperature is from 25 to 100° C. Although solvent is not required it may be used to facilitate the heat and mass transfer. The reaction of the polyacrylate ester with the amine is preferably carried out in an inert gas atmosphere, for example, under nitrogen or argon, to prevent or minimize unwanted side reactions. However, this is not necessary for a successful reaction. The reaction can be carried out at a temperature of from about −30° C. or lower to about 150° C. or higher. The preferred temperature range is from about −10° C. to about 75° C. and the most preferred range is from about 15° C. to about 60° C. The pressure of the reaction system can be maintained at atmospheric pressure or superatmospheric pressure.

To prevent acrylate polymerization various inhibitors or stabilizers may also be used during the reaction. Typical inhibitors such as hydroquinone, hydroqinone methyl ether, butylated hydroqinone can be used.

Solvent may be used to facilitate heat and mass transfer during the reaction which was exothermic. Non-reactive solvents such as hydrocarbons, esters, and halogenated solvents may be used. Examples are toluene, hexane, heptane, ethyl acetate, butyl acetate, chloroform, chlorobenzene. The reaction can be carried out in the absence of a solvent or in the presence of an inert solvent. Among the suitable inert organic solvents that can be used one can mention methanol, ethanol, acetone, benzene, toluene, xylene, hexane, octane, and the like. Any inert solvent can be used that does not interfere with the reaction. In order to minimize side reactions, the reaction is preferably carried out in the absence of light.

In the reaction, one or more of the acrylyl groups of the polyacrylate ester reacts to displace the amino hydrogen atom while the rest of acrylyl group of the polyacrylate ester is not affected. The molar amount of arnines charged to the reaction system can vary from about 0.9 mole to about 3 moles or more per mole of polyacrylates to produce the oligomers.

In carrying out the reaction the polyacrylate ester can be added to the amino compound or the amino compound can be added to the polyacrylate ester; the latter procedure is preferred. At the completion of the reaction, the amine acrylates are recovered as residue products; however, in some instances recovery by conventional distillation and fractionation procedures is possible. The amine acrylates can also be prepared by simultaneously spraying separate streams of the amine compound and the polyacrylate ester onto a surface or into an enclosed area. In many instances the reaction is rapid and the two components quickly co-react. The means for simultaneously feeding two or more separate streams in the proper ratios are known in the art and such equipment does not constitute a part of this invention.

The final products have both acrylate and amine functionality with the following general structure:

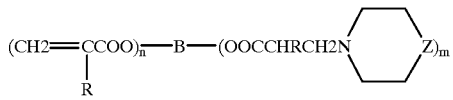

where R is hydrogen or methyl, B is the residue of a polyol, Z is oxygen, $CH_2$, or nitrogen containing group, n is an integer of 1 to 6, and m is an integer of 1 to 5.

These acrylates were found to be very effective synergists in UV/EB curing and can be used alone or along with other acrylate monomers and oligomers. In the present invention the aminopolyacrylates were evaluated as part of the formulation vs some commercial products. The results showed that these new polymerizable synergists are very effective and higher activity was observed. As previously indicated, the amine acrylates are readily cured by ultraviolet light radiation or electron beam radiation or high intensity predominantly continuum light radiation. The curing is very rapid and a durable protective film is formed.

The coating compositions can be applied to a surface by any of the known conventional means, including the spray, curtain, dip, pad and roll-coating techniques. The substrate to be coated can be any composition; for example, wood, metal, paper, plastic, fabric, fiber, ceramic, concrete, plaster, glass, etc.

The amine acrylate-containing compositions can be cured by ionizing radiation, either particulate or non-particulate, or non-ionizing radiation. As a suitable source of particulate radiation, one can use any source which emits electrons or charged nuclei.

The use of low to high pressure mercury lamps to generate ultraviolet light is known. The cure time depends on the light intensity and the specific formulation. An appreciable period of time is generally needed for completion of a reaction when a material is exposed to the low intensity ultraviolet radiation generated from a mercury lamp.

The rate of curing can be enhanced by the addition of suitable photosensitizers and photoinitiators. Illustrative of suitable photosensitizer compounds one can mention acetophenone, propiophenone, benzophenone, xanthone, fluorenone, benzaldehyde, fluorene, anthraquinone, triphenylamine, carbazole, 3- or 4-methylacetophenone, 3- or 4-pentylacetophenone, 3- or 4-methylbenzophenone, 3- or 4-chlorobenzophenone, 4,4'-bis(dimethylamino) benzophenone, 4,4'-dimethoxybenzophenone, 4-chloro-4'-benzylbenzophenone, 3-chloroxanthone, 3,9-dichloroxanthone, 3-chloro-8-nonylxanthone, 3-methoxyxanthone, 3-iodo-7-methoxyxanthone, and the like. As is obvious one can use a mixture of photosensitizers. Examples of photoinitiators are 1-hydroxycyclohexyl phenyl ketone, 2-benzyl-2-N,N-dimethylamino-1-(4-morpholinophenyl)-1-butanone, 1-hydroxycyclohexyl phenyl ketone, 2,2-dimethoxy-2-phenyl acetophenone, and 2-hydroxy-2-methyl-1-phenyl-propan-1-one. The amount of photosensitizer or photoinitiator used can vary from about 0.01 to about 20 weight percent of the coating solution. A preferred amount is from about 0.1 to about 5 weight percent, and most preferred is a concentration of from about 0.5 to about 3 weight percent. A mixture of photosensitiser and/or photoinitiators can also be used.

As previously indicated the amine acrylates, singly or in mixtures, can be blended with from 1 to about 50 weight percent or more of other coating compositions that are known to cure on exposure to radiation. The concentration of amine acrylates blended in such compositions can vary from about 1 to 99.9 weight percent of the coating composition, preferably from about 10 to about 75 weight percent. These coating compositions can also contain from about 5 to about 50 weight percent of a polymerizable solvent such as styrene or a high boiling acrylyl ester.

The coating compositions are produced by mixing the selected components thereof by conventional known methods. The blend can be heated, if desired, to facilitate mixing.

Coating compositions having the amine acrylate compound present, alone or in admixture, can contain fillers, pigments and other additives conventionally present in coating compositions. These additives are so well known to those skilled in the art that they need no specific mention; nor is it necessary for an understanding of this invention to recite concentrations thereof. The same can be said of the known radiation curable coating compositions that can be admixed with the amine acrylates to improve the curing and crosslinking properties.

EXAMPLES

The following non-limiting examples are presented to illustrate a few embodiments of the invention. All parts and percentages are by weight unless otherwise indicated.

Procedure for UV cure formulation:

Coating Formulations: All components were weighed into amber glass jars and heated in a 60° C. forced-air oven before mixing on an electric stirrer at moderate speed.

Substrate: Leneta form 2A.

Application: The coatings were cured using one 600 watt/inch Fusion H lamp at full power in air at the lamp height at 50 fpm line speed. The line speed was varied for the surface cure measurements.

Surface Cure Speed: The surface cure speed was determined by using both a wooden tongue depressor and the back of a fingernail. The tongue depressor was lightly scratch across the surface of the coating using its edge. Moderate pressure was also used in the fingernail scratch test. Both tests gave the same results. The fastest line speed (in 10 fpm increments, in the 40–1000 fpm range) was reported where no mark was apparent on the coated surface MSCS stands for Maximum Surface Cure Speed.

MEK Double Rubs: MEK double rubs were determined using panels that were cured at 50 fpm. The test was run over the black section of the Leneta chart using moderate pressure.

Example 1

In a reactor, 226.0 g of hexanediol diacrylate was placed. Morpholine (87.0 g) was added slowly under stirring, exothermic reaction took place as indicated by temperature increase. The reaction was kept at 50° C. for 4 hours. A clear, light yellow liquid was obtained.

Example 2

Example 1 was repeated with 85.0 g of piperidine instead of morpholine. Similar result was obtained.

Example 3

Example 1 was repeated using 428.0 g of ethoxylated trimethylolpropane triacrylate (Sartomer SR454) instead of hexanediol diacrylate. The reaction was kept at 50° C. for 4 hours which resulted in a clear, light yellow liquid.

Example 4

Example 1 was repeated using 428.0 g of propoxylated glycerol triacrylate (Sartomer SR9020) instead of hexanediol diacrylate.

Example 5

Example 1 was repeated with trimethylolpropane triacrylate instead of hexanediol diacrylate.

Example 6

In a reactor, 300.0 g of tripropylene glycol triacrylate was placed and air sparge was applied. Morpholine (136.8 g) was added slowly under stirring, exothermic reaction took place as indicated by temperature increase. The reaction was kept at 50° C. for 4 hours. A clear, light yellow liquid was obtained.

Example 7

In a reactor, 296.0 g of trimethylolpropane triacrylate was placed and air sparge was applied. Morpholine (174.0 g) was added slowly under stirring, exothermic reaction took place as indicated by temperature increase. The reaction was kept at 50° C. for 4 hours. A clear, light yellow liquid was obtained.

Example 8

In a reactor, 428.0 g of ethoxylated trimethylolpropane triacrylate (Sartomer SR454) was placed and air sparge was applied. Morpholine (174.0 g) was added slowly under stirring, exothermic reaction took place as indicated by temperature increase. The reaction was kept at 50° C. for 4 hours. A clear, light yellow liquid was obtained.

Example 9

In a reactor, 450.0 g of propoxylated glycerol triacrylate (Sartomer SR9021) was placed and air sparge was applied. Morpholine (136.6.0 g) was added slowly under stirring, exothermic reaction took place as indicated by temperature increase. The reaction was kept at 50° C. for 4 hours. A clear, light yellow liquid was obtained.

Example 10

UV cure study of various aminoacrylates

Some of the products from the above samples were tested in the specified formulations at two different levels and both surface cure and MEK double rubs (solvent resistance) were measured.

| CN120 (g) | SR351 (g) | SR306 (g) | BP (g) | AA | New AA (g) | MSCS, fpm | MEK |
|---|---|---|---|---|---|---|---|
| 34 | 26 | 33 | 5 | MDEA | 4.7 | 100 | 200+ |
| 34 | 26 | 33 | 5 | EBP104 | 4.7 | 70 | 200+ |
| 34 | 26 | 33 | 5 | EBP101 | 4.7 | 50 | 200+ |
| 34 | 26 | 33 | 5 | EBP115 | 4.7 | 90 | 200+ |
| 34 | 26 | 33 | 5 | E6 | 4.7 | 110 | 200+ |
| 34 | 26 | 33 | 5 | E7 | 4.7 | 100 | 200+ |
| 34 | 26 | 33 | 5 | E8 | 4.7 | 100 | 200+ |
| 34 | 26 | 33 | 5 | E9 | 4.7 | 90 | 200+ |
| 34 | 26 | 33 | 5 | MDEA | 9.3 | 120 | 200+ |
| 34 | 26 | 33 | 5 | EBP104 | 9.3 | 110 | 200+ |
| 34 | 26 | 33 | 5 | EBP101 | 9.3 | 100 | 200+ |

| CN120 (g) | SR351 (g) | SR306 (g) | BP (g) | AA | New AA (g) | MSCS, fpm | MEK |
|---|---|---|---|---|---|---|---|
| 34 | 26 | 33 | 5 | EBP115 | 9.3 | 160 | 200+ |
| 34 | 26 | 33 | 5 | E6 | 9.3 | 180 | 200+ |
| 34 | 26 | 33 | 5 | E7 | 9.3 | 200 | 200+ |
| 34 | 26 | 33 | 5 | E8 | 9.3 | 180 | 200+ |
| 34 | 26 | 33 | 5 | E9 | 9.3 | 170 | 200+ |

CN120 is bisphenol A diglycidyl ether diacrylate (Sartomer Company, Inc. brand)
SR351 is trimethylolpropane triacrylate (Sartomer brand).
SR306 is tripropylene glycol diacrylate (Sartomer brand).
BP is benzophenone
AA—aminoacrylate
MSCS—maximum surface cure speed.
MEK—MEK double rubs for testing solvent resistance.
MDEA is methyl diethanol amine.
EBP101 is diethylamine and tripropylene glycol diacrylate adduct (UCB Radcure brand).
EBP104 is diethylamine and hexanediol diacrylate adduct (UCB Radcure brand).
EBP115 is Diethylamine and propoxylated glycerine triacrylate adduct (UCB Radcure brand).
E6, E7, E8, and E9 are materials prepared from Examples 6, 7, 8, and 9 respectively.

While the invention has been described and exemplified in detail, various alternative embodiments should become apparent to those skilled in this art without departing from the spirit and scope of the invention.

What is claimed is:

1. (Meth)acrylate functional compound which is the reaction product of a cyclic secondary amine selected from the group consisting of morpholine, substituted morpholines, piperidine, and substituted piperidines and a poly(meth)acrylate having at least three (meth)acrylate groups, wherein the molar ratio of secondary amine to (meth)acrylate in the reactants is at least 0.9, said compound being useful for radiation curable coating or ink composition having low viscosity, low volatility, and high cure rate under radiation, the compound being water insoluble.

2. Compound according to claim 1 wherein the cyclic secondary amine is selected from the group consisting of morpholine and piperidine.

3. Composition useful for radiation cured coatings and inks comprising a compound according to claim 1 and one or more other acrylate compounds, said composition having low viscosity, low volatility, and exhibiting a high cure rate.

4. A cured coating or ink prepared by radiation curing a composition according to claim 3.

5. Coated or printed article having a cured coating or ink of claim 4.

6. Composition of claim 3, further including a photopolymerization initiator.

7. A cured coating or ink prepared by radiation curing the of claim 6.

8. A process for preparing a cured coating on a substrate comprising applying the composition of claim 3 to the substrate and exposing the composition to ultraviolet radiation.

* * * * *